United States Patent [19]

Krohn et al.

[11] Patent Number: 4,613,464
[45] Date of Patent: Sep. 23, 1986

[54] PROCESS FOR THE PREPARATION OF ANTHRACYCLINONES

[75] Inventors: Karsten Krohn, Brunswick; Bert Behnke, Ahrensburg, both of Fed. Rep. of Germany

[73] Assignee: Hoechst Aktiengesellschaft, Fed. Rep. of Germany

[21] Appl. No.: 639,311

[22] Filed: Aug. 10, 1984

[30] Foreign Application Priority Data

Aug. 12, 1983 [DE] Fed. Rep. of Germany ....... 3329185

[51] Int. Cl.$^4$ .................... C07C 49/423; C07C 50/22; C07C 50/24
[52] U.S. Cl. ................................. 260/384; 260/351.5
[58] Field of Search ............... 260/351.5, 384, 369, 260/396 R, 365, 351.1

[56] References Cited

U.S. PATENT DOCUMENTS 4,215,062 7/1980 Mitscher ......................... 260/369
4,312,811 1/1982 Schoemans et al. ............. 260/369
4,536,336 8/1985 Kishi ............................... 260/351.1

*Primary Examiner*—Richard L. Raymond
*Assistant Examiner*—Raymond Covington
*Attorney, Agent, or Firm*—Finnegan, Henderson, Farabow, Garrett & Dunner

[57] ABSTRACT

The present invention relates to a new process for the preparation of anthracyclinones of the formula

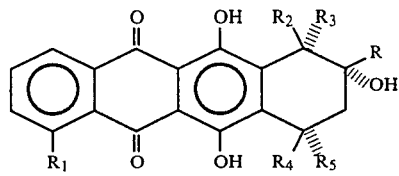

in which R denotes $C_1$–$C_4$-alkyl, $R_1$ denotes H or OH, and $R_2$ and $R_3$ are different and each represent H or OH, and $R_4$ and $R_5$ are different and each represent H or OH, starting from a compound of the formula

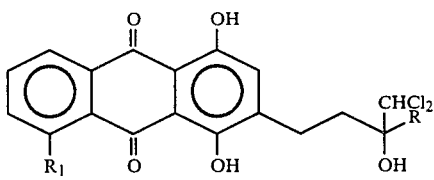

in which $R_1$ and R have the abovementioned meaning.

The compounds of the formula I are valuable intermediates in the preparation of the corresponding glycosides having cytostatic efficacy.

5 Claims, No Drawings

PROCESS FOR THE PREPARATION OF ANTHRACYCLINONES

The present invention relates to a new process for the preparation of anthracyclinones of the formula

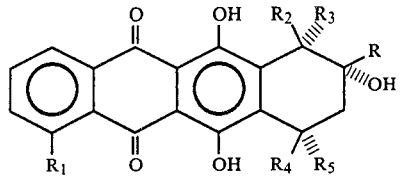

in which R denotes $C_1$-$C_4$-alkyl and $R_1$ denotes H or OH, $R_2$ and $R_3$ are different and each represent H or OH, and $R_4$ and $R_5$ are different and each represent H or OH.

The process comprises taking a compound of the formula

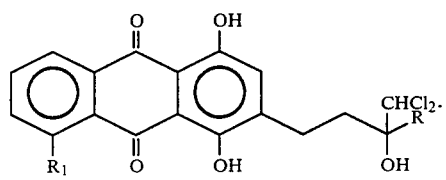

in which $R_1$ and R have the abovementioned meanings, and either (a) where $R_1$ denotes hydrogen, reacting it with an alkali metal hydroxide solution with the addition of a reducing agent, preferably sodium dithionite, at 0° C. and then oxidizing the resulting product with air and acidifying, whereupon a compound of the formula III

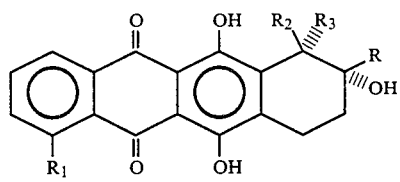

in which $R_1$ denotes hydrogen and R, $R_2$ and $R_3$ have the abovementioned meaning, is obtained or (b) where $R_1$ denotes the OH group, reacting it in a phase-transfer reaction with an alkali metal hydroxide solution in a chlorinated hydrocarbon, preferably dichloromethane, with the addition of tetrabutylammonium hydrogen sulfate, followed by reduction with a suitable reducing agent, preferably sodium dithionite, at 0° C. to give a compound of the formula III, in which $R_1$ denotes the OH group and $R_1$, $R_2$ and $R_3$ have the abovementioned meaning, or (c) where $R_1$ denotes the OH group and R denotes $CH_3$, reacting it with an alkali metal methanolate at room temperature under an inert gas to give a compound of the formula IV

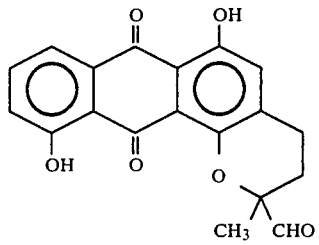

and converting the resulting cyclic aldehyde, by reaction with a suitable reducing agent, preferably sodium dithionite, at 0° C. followed by oxidation with air and acidification, into a compound of the formula III, in with R denotes $CH_3$ and $R_2$ and $R_3$ have the abovementioned meaning, and (d) converting a compound of the formula III, in which R, $R_1$ and $R_3$ have the abovementioned meaning, and $R_2$ denotes the OH group by esterification with hexafluoroacidic anhydride into a compound of the formula III, in which $R_2$ represents the $-OCOCF_3$ radical, and (e) brominating a compound of the formula III, in which R and $R_1$ have the abovementioned meaning, $R_3$ represents hydrogen and $R_2$ represents the $-OCOCF_3$ radical, by customary methods and then carrying out hydrolysis to give a compound of the formula I.

The compound of the formula II in which $R_1$ denotes hydrogen is converted into the labile aldehyde of the formula V

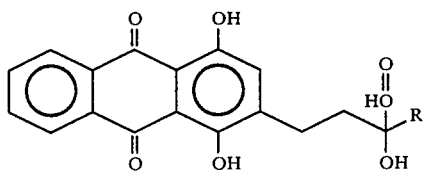

using an alkali metal hydroxide solution, for example using 1N potassium hydroxide solution, at about 25° C. For this, the compound of the formula II is advantageously partially dissolved in methanol before the metal hydroxide solution is added under nitrogen. The aldehyde, which is produced virtually quantitatively after about 10 min., is not isolated and is reduced with sodium dithionite at 0° C. to give the leuco form. After oxidation with air and acidification, the cyclic compound of the formula III is obtained.

Separation of the trans and cis diols of the formula III can be carried out via the readily soluble acetonides of the formula VI

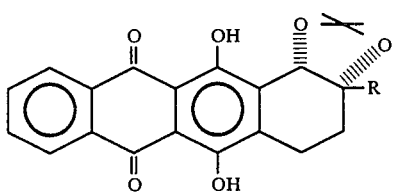

which are prepared quantitatively by treatment of the crude product of the cyclization with acetone/p-toluenesulfonic acid.

Where $R_1$ in formula II denotes the OH group, the hydrolysis of the dichlorides is carried out by a phase-transfer reaction. For this, the -hydroxydichlorides are converted within one hour quantitatively into the corresponding aldehydes in a system comprising a chlorinated hydrocarbon, preferably dichloromethane, and an alkali metal hydroxide solution, for example 0.2N NaOH, with the addition of tetrabutylammonium hydrogen sulfate. The labile aldehydes are not isolated and are converted by reduction with a suitable reducing agent, preferably sodium dithionite, at 0° C., into the tetracyclic compounds of the formula III. It is also possible to convert an -hydroxydichloride of the formula II, in which $R_1$ denotes OH and R denotes $CH_3$, into the cyclic aldehyde of the formula IV by treatment with alkali metal alkanolate, preferably sodium methanolate, at room temperature under inert gas. This aldehyde, which is likewise labile, can be converted in high yields into the tetracyclic compound of the formula III by using a suitable reducing agent, preferably sodium dithionite, at 0° C., followed by oxidation with air and acidification.

The introduction of the OH group into the 10-position is carried out by the customary methods of radical bromination. However, for this purpose, the transhydroxy group on C-7 ($R_2$=OH) must be protected by conversion into the trifluoroacetate, which is carried out by esterification with hexafluoroacetic anhydride. The resulting trifluoroacetate is brominated in an inert chlorinated hydrocarbon, for example carbon tetrachloride, under the action of light at room temperature for 1-5 hours, preferably 2-3 hours. The resulting mixture of the labile bromides is not isolated and is reacted in a two-phase system comprising ether and ice-cold alkali metal hydroxide solution, for example 1N sodium hydroxide solution. After acidification, the 8,10-diol of the formula I is obtained.

The starting materials and intermediates of the formula II can be prepared in the following manner:

Lithium dichloromethane is added onto a compound of the formula VII

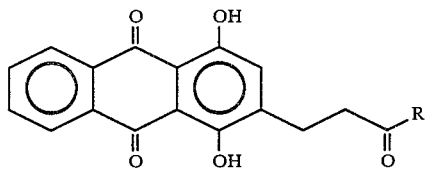

in which R represents $C_1$–$C_4$-alkyl, at temperatures of −90° to −100° C. The reaction is carried out such that the dichloromethane is metalated with n-butyllithium in tetrahydrofuran at about −100°·C., and the ketone of the formula VII is reacted with the carbenoid at this temperature. The subsequent neutralization of the reaction mixture is likewise carried out at −90° C. to −100° C. The compounds of the formula II are obtained in this reaction with yields between 90 and 95%.

The syntheses hitherto known of anthracyclinones are based either on the Diels-Alder reaction (A. S. Kende and Y. Tsay, J. Chem. Soc., Chem. Commun. 1977, 140; and K. Krohn and A. Rösner, Liebigs Ann. Chem. 1979, 2,018) or on an intramolecular variant of the Marschalk reaction (C. Marschalk, F. Krenig and N. Ouronsoff, Bull. Soc. Chim. Fr. 3 (1936), 1,545). However, several stages are necessary in these reactions, for example a three-stage reaction sequence is necessary to cleave the α-hydroxydithioacetals. A further disadvantage takes the form of a diminution in the yields from the preparation of the appropriate α-hydroxyaldehydes using lithiated 1,3-dithian due to partial reduction to give the leuco-anthraquinones. In contrast, the process according to the invention leads, in a one-pot reaction, from the compounds of the formula II to the anthracyclinones of the formula III with yields of 80%.

The compounds of the formula I can be converted by customary routes, by substitution in the 7- and/or 10-position, into the corresponding glycosides having cytostatic (antitumoral) efficacy (see, for example, U.S. Pat. Nos. 3,988,315 and 4,071,411, corresponding to German Pat. No. 2,532,568).

EXAMPLES

Melting points (uncorrected): apparatus supplied by Elektrothermal. IR spectra: Perkin-Elmer 297 apparatus. UV spectra (in methanol): Zeiss DMR 10 spectrophotometer. $^1$H-NMR spectra (tetramethylsilane as internal standard): Bruker WH 270 (270 MHz) and WH 400 (400 MHz) or Perkin-Elmer R 32 (90 MHz); sorbent $CDCl_3$). MS: m/e=Varian CH 7 MAT apparatus (70 ev); RDA denotes retro-Diels-Alder fragment.

General procedure for the synthesis of the α-hydroxydichlorides (II)

23:3 ml of 1.6N butyllithium were added, within 30 minutes, to a mixture of 150 ml of tetrahydrofuran and 3.06 g (36 mmol) of dichloromethane at −100° C. After a further 30 min. at −100° C., a solution of the appropriate ketone (VII) was added over a period of 1-2 hours; the temperature during this was not permitted to exceed −95° C. After 1 hour at −100° C., the solution was cautiously neutralized with 6N hydrochloric acid and, after warming to room temperature, 200 ml of dichloromethane were added. The solution was washed three times with water, dried over sodium sulfate and evaporated in vacuo, and the residue was crystallized from a little dichloromethane.

EXAMPLE 1

1,4-Dihydroxy-2-(4,4-dichloro-3-hydroxy-3-methyl-butyl)-9,10-anthraquinone (II):

1.90 g (95%) was obtained from 1.59 g (5.1 mmol) of ketone (VII, R=$CH_3$) and had a melting point of 148° C., IR: 3440 (OH), 1620 (chelated quinone), 1585 (C=C). −UV λmax (lgε)=226 (4.39), 246 (4.65), 279 (4.10), 318 (3.71), 456 (4.04), 478 (4.07), 508 nm (3.90). -$^1$H-NMR:=1.48 (s; 3H, $CH_3$), 2.09 (cm; 2H, 2'—$CH_2$), 2.32 (s; 1H, OH), 2.89 (cm; 2H, 1'—$CH_2$), 5.74 (s; 1H, $CHCl_2$), 7.16 (s; 1H, 3—H), 7.80 (cm; 6—, 7—H), 8.31 (cm; 2H, 5—, 8—H), 12.90, 13.39 (each s; 1H each, each OH).

$C_{19}H_{16}O_5Cl_2$ (395.2): calculated: C 57.74, H 4.07, Cl 17.94, found: C 57.81, H 4.02, Cl 18.18.

EXAMPLE 2

1,4-Dihydroxy-2-(3-dichloromethyl-3-hydroxypentyl)-9,10-anthraquinone (II):

655 mg (91%) was obtained from 570 mg (1.76 mmol) of ketone (VII, R=$C_2H_5$) and had melting point 119° C. IR: 3450 (OH), 1620 (chelated quinone), 1585 (C=C), region 800-720 cm$^{-1}$ (C—Cl). −UV: λmax (lgε)=225 (4.27), 246 (4.51), 281 (3.97), 317 (3.43), 456 (3.93), 477 (3.97, 510 nm (3.77). -$^1$H-NMR:=1.04 (t; J=7.6 Hz; 3H, CH$_3$), 1.93 (q; J=7.6 Hz; 2H, CH$_2$CH$_3$), 2.10 (cm; 2H, 2'—CH$_2$), 2.22 (s; 1H, OH), 2.85 (cm; 2H, 1'—CH$_2$), 5.91 (s; 1H, CHCl$_2$), 7.19 (s; 1H, 3—H), 7.83 (cm; 2H, 6—, 7—H), 8.34 (cm; 2H, 5—, 8—H), 12.94, 13.42 each s; 1H each, each OH).

C$_{20}$H$_{18}$O$_5$Cl$_2$ (409.3): calculated: C 58.70, H 4.43, Cl 17.32, found: C, 58.99, H 4.47, Cl 17.39.

EXAMPLE 3

3-(4,4-Dichloro-3-hydroxy-3-methylbutyl)-1,4,5-trihydroxy-9,10-anthraquinone (II)

771 mg (94%) are obtained from 650 mg of ketone (VII, R=CH$_3$) (see below) and had melting point 201° C. (decomposition). IR: 3450 (OH), 2960, 2925 (CH), 1600 (chelated quinone, C=C). —UV: $\lambda_{max}$ (lg$\epsilon$)=229 (4.54), 245 (4.23), 285 (3.81), 460 (3.94), 487 (4.05), 508 (3.93), 520 nm (3.86). -$^1$H-NMR:=1.55 (s; 3H, CH$_3$), 2.09 (cm; 2H, 2'—H$_2$), 2.19 (s; 1H, OH), 2.90 (cm; 2H, 1'—H$_2$), 5.79 (s; 1H, CH—Cl$_2$), 7.22 (s; 1H, 2—H), 7.31 (dd, J$_{6,7}$=8.2, J$_{6,8}$=1.2 Hz; 1H, 6—H), 7.71 (dd, J$_{6,7}$=8.2, J$_{7,8}$=7.6 Hz; 1H, 7—H), 7.89 (dd, J$_{7,8}$=7.6, J$_{6,8}$=1.2 Hz; 1H, 8—H), 12.23, 12.81, 13.09 (each s; 1H each, each OH).

C$_{19}$H$_{16}$O$_6$Cl$_2$ (411.2): calculated: C 55.50, H 3.92, Cl 17.24, found: C 55.24, H 3.87, Cl 17.13.

EXAMPLE 4

3-(3-Dichloromethyl-3-hydroxypentyl)-1,4,5-trihydroxy-9,10-anthraquinone (II)

805 mg (92%) are obtained from 700 mg of ketone (VII, R=C$_2$H$_5$) and had melting point 174° C. IR: 3475 (OH), 2960, 2930, 2880 (CH), 1600 (chelated quinone, C=C). UV: $\lambda_{max}$ (lg$\epsilon$)=288 (4.58), 245 (4.34), 284 (3.97), 461 (3.99), 487 (4.07), 510 (3.96), 520 nm (3.91). $^1$H-NMR:=1.04 (t, J=7.4 Hz; 3H, CH$_3$), 1.93 (q, J=7.4 Hz; 2H, CH$_2$CH$_3$), 2.09 (cm; 2H, 2'—H$_2$), 2.15 (s; 1H, OH), 2.85 (cm; 2H, 1'—H$_2$), 5.91 (s; 1H, CH—Cl$_2$), 7.22 (d, J=0.5 Hz; 1H, 2—H), 7.31 (dd, J$_{6,7}$=8.4, J$_{6,8}$=1.2 Hz; 1H, 6—H), 7.71 (dd, J$_{6,7}$=8.4, J$_{7,8}$=7.6 Hz, 7—H), 7.89 (dd, J$_{7,8}$=7.6, J$_{6,8}$=1.2 Hz; 1H, 8—H), 12.22, 12.80, 13.09 (each s; 1H each, each OH).

C$_{20}$H$_{18}$O$_6$Cl$_2$ (425.3): calculated: C 56.49, H 4.27, Cl 16.67, found: C 56.28, H 4.21, Cl 16.63.

EXAMPLE 5

3-(3-Dichloromethyl-3-hydroxyhexyl)-1,4,5-trihydroxy-9,10-anthraquinone (II):

1.10 g (89%) is obtained from 1.00 g of ketone (VII, R=n—C$_3$H$_7$) and had melting point 175° C. (decomposition). IR: 3475 (OH), 2960, 2920, 2870 (CH), 1600 (chelated quinone, C=C). UV: $\lambda_{max}$ (lg$\epsilon$)=232 (4.57), 250 (4.33), 290 (3.89), 434 (3.72), 462 (4.01), 479 (4.07), 489 (4.11), 511 (3.99), 523 nm (3.95). $^1$H-NMR:=1.01 (t, J=7.2 Hz; 3H, CH$_3$), 1.49 (cm; 2H, CH$_2$CH$_2$CH$_3$), 1.84 (cm; 2H, CH$_2$CH$_2$CH$_3$), 2.09 (cm; 2H, 2'—H$_2$), 2.16 (s; 1H, OH), 2.85 (cm; 1'—H$_2$), 5.88 (s; 1H, CH—CL$_2$), 7.22 (s; 1H, 2—H), 7.31 (dd, J$_{6,7}$=8.4, J$_{6,8}$=1.2 Hz; 1H, 6—H), 7.71 (t; 1H, 7—H), 7.89 (dd, J$_{7,8}$=7.6, J$_{6,8}$=1.2 Hz; 1H, 8—H), 12.21, 12.79, 13.07 (each s; 1H each, each OH).

C$_{21}$H$_{20}$O$_6$Cl$_2$ (439.3): calculated: C 57.42, H 4.59, Cl 16.14, found: C 57.31, H 4.52, Cl 16.03.

EXAMPLE 6:

(+)-1-Deoxy-1-rhodomycinone (III, R=CH$_3$, R$_2$=OH, R$_3$=H)

100 ml of 1N potassium hydroxide solution were added to a solution of 1.9 g (4.81 mmol) of dichloride (II, R=CH$_3$) in 40 ml of methanol at room temperature under nitrogen, and the mixture was stirred for 10 min. It was then cooled to 0° C., and sodium dithionite solution was added until the color changed from blue to orange (about 5 mmol) and the mixture was stirred at 0° C. for 20 min. Air was passed in the vigorously stirred solution for the oxidation. The product mixture was precipitated by acidification with cold 6N hydrochloric acid. The mixture was extracted twice with 300 ml of dichloromethane each time, and the solution was washed with water, dried over sodium sulfate, filtered and the solvent was removed by evaporation. The crude product (cis/trans mixture: yield 1.4 g) was taken up in 100 ml of acetone, 30 mg of p-toluenesulfonic acid were added, and the mixture was allowed to stand at room temperature for five hours. Then 300 ml of water were added and the mixture was extracted with 150 ml of dichloromethane. The organic phase was washed twice with water, dried over sodium sulfate, filtered and the filtrate was evaporated to 8 ml in vacuo. 1.0 g (61%) of the sparingly soluble trans-diol (=title compound) crystallized (12 hours, 4° C.) and had melting point 246° C. (decomposition). The rhodomycinone was identical with a sample prepared earlier (K. Krohn and B. Behnke, Liebigs Ann. Chem. 1979, 2,011).

EXAMPLE 7

Isopropylidene ether (VI, R=CH$_3$)

The isopropylidene ether of the cis-diol (III, R=CH$_3$, R$_2$=H, R$_3$=OH) was present in the mother liquor (see above), and this was crystallized by addition of a little petroleum ether, and the product was identical with a reference sample. Yield 452 mg (25%); melting point 152° C.

EXAMPLE 8

(+)-1-Deoxy-7-epi-$\beta_1$-rhodomycinone (III, R=CH$_3$, R$_2$=H, R$_3$=OH)

0.2 ml of concentrated hydrochloric acid was added to a solution of 3.8 mg (0.1 mmol) of the acetonide (Example 7) in tetrahydrofuran/methanol, and the mixture was evaporated to dryness after 4 hours. Quantitative yield; melting point 203° C. (decomposition).

EXAMPLE 9

(+)-1-Deoxy-$\lambda$-rhodomycinone (III, R=C$_2$H$_5$, R$_2$=OH, R$_3$=H) .

250 mg (0.61 mmol) of dichloride (II, R=C$_2$H$_5$) were reacted as described in Example 6. Yield 136 mg (63%); melting point 214° C. IR: 3520 (OH), 1610 (chelated quinone), 1580 (C=C). UV: $\lambda_{max}$ (lg$\epsilon$)=249 (4.45), 284 (3.76), 456 (3.79), 480 (3.86), 514 nm (3.70). $^1$H-NMR: (pyridine-d$_5$, TMS=O) $\delta$=1.38 (t; J=7.6 Hz; 3H, CH$_3$), 2.13 (cm; 2H, CH$_2$CH$_3$, 9a—H), 2.32 (cm; 1H, CH$_2$CH$_3$, 9a—H), 2.32 (cm; 1H, CH$_2$CH$_3$), 2.41 (dddd; J$_{gem}$=13.8, J$_{9e,10a}$=6.4, J$_{9e,10e}$=3.6, J$_{9e,7e}$=1.2 Hz; 1H, 9e—H), 3.25 (cm; 2H, 10a, e—H), range 4.92-6.09 (broad signal; 2H, 2OH), 5.49 (d; J$_{9e,7e}$=1.2 Hz; 1H, 7—H), 7.71 (cm; 2H, 2—, 3—H), 8.36 (cm; 2H, 1—, 4—H), 13.83, 14.17 (each s; 1H each, each OH). MS (195° C.): m/e=354 (M+, 53%), 336 (30), 307 (15), 284 (11), 282 (RDA, 33), 280 (24), 279 (44), 255 (18), 254 (100), 239 (16).

$C_{20}H_{18}O_6$ (354.4): calculated: C 67.79, H 4.56, found: C 67.48, H 4.60.

EXAMPLE 10 cis-3a-Ethyl-6,13-dihydroxy-2,2-dimethyl-3a,4,5,7,12,13b-hexahydronaphthaceno|1,2-d|-1,3-dioxole-7,12-dione (VI, $R=C_2H_5$)

55 mg (23%) of the acetonide crystallized out of the mother liquor (see above) after addition of a little petroleum ether and had a melting point of 300° C. IR: 1620 (chelated quinone), 1580 (C=C). UV: $\lambda_{max}$ (Lgε)=230 (4.19), 234 (4.21), 251 (4.17), 285 (3.65), 292 (3.65), 317 (3.33), 472 (3.49), 482 (3.51), 506 nm (3.37). $^1$H-NMR: δ=1.01 (t; J=7.4 Hz; 3H, CH$_2$CH$_3$), 1.32 (s; 3H, CH$_3$), 1.53 (s; 3H, CH$_3$), 1.64 (cm; 2H, CH$_2$CH$_3$), 1.71 (dt; $J_{gem}$=14.2, J=4.8 Hz; 1H, 9—H), 2.14 (ddd, $J_{gem}$=14.2, J=6.4, J=5.5 Hz; 1H, 9—H), 2.90 (cm; 2H 10—H), 5.17 (s; 1H, 7a—H), 7.83 (cm; 2H, 2—, 3—H), 8.36 (cm; 2H, 1-, 4-H), 13.38, 13.64 (each s; 1H each, each OH). MS (255° C.): m/e=395 (M+1, 17%), 394 (M+, 67%), 379 (36), 338 (17), 337 (78), 336 (56), 321 (12), 320 (15), 319 (43), 318 (18), 309 (21), 308 (100), 307 (60), 293 (12), 291 (16), 290 (14), 281 (17), 280 (52), 279 (28), 187 (35).

EXAMPLE 11

(+)-1-Deoxy-7-epi-γ-rhodomycinone (III, $R=C_2H_5$, $R_2=H$, $R_3=OH$)

2 ml of 6N hydrochloride acid were added to a solution of 50 mg of acetonide according to Example 10 (0.13 mmol) in 10 ml of tetrahydrofuran at room temperature, and the mixture was stirred for 12 hours. It was then diluted with water, extracted with dichloromethane, and the organic phase was dried over sodium sulfate, filtered and the filtrate was evaporated in vacuo. 44 mg (99%) of cis-diol crystallized out whith dichloromethane and had melting point 239° C. IR: 3400 (OH), 1620 (chelated quinone), 1580 (C=C). UV: $\lambda_{max}$ (lgγ)=248 (4.46), 285 (3.84), 457 (3.83), 477 (3.90), 509 (3.71), 562 (2.93). $^1$H-NMR: δ=1.03 (t; J=7.4 Hz; 3H, CH$_2$CH$_3$), 1.62 (dq; $J_{gem}$=21.0, J=7.4 Hz; 2H, CH$_2$CH$_3$), 1.76 (dt; $J_{gem}$=6.6 Hz; 1H, 9—H), 2.10 (ddd, $J_{gem}$=13.4, J=7.0, J=6.0 Hz; 1H, 9—H), 2.76 (ddd, $J_{gem}$=19.2, J=7.4, J=6.0 Hz; 1H, 10—H), 2.80 (s; 1H, OH), 3.05 (dt, $J_{gem}$=19.2, J=7.2 Hz; 1H, 10—H), 3.82 (broad s; 1H, OH), 4.82 (broad s; 1H, 7—H), 7.85 (cm; 2H, 2—, 3—H), 8.36 (cm; 2H, 1—, 4—H), 13.35, 13.90 (each s; 1H each, each OH). MS (210° C.): m/e=354 (M+, 15%), 336 (7), 282 (RDA, 9), 279 (12), 254 (26).

EXAMPLE 12

(+)-1,7-Dideoxy-7-rhodomycinonyl trifluoroacetate (III, $R=CH_2CH_5$, $R_2=OCOCF_3$, =H)

After 5 hours at 20° C., a solution of 50 mg (0.14 mmol) of (±)-1-deoxy-β$_1$-rhodomycinone (Example 6) in 3 ml of hexafluoroacetic anhydride was evaporated to dryness in vacuo, and the residue was crystallized from dichloromethane/petroleum ether. Yield 61 mg (98%); melting point 164° C. IR: 3500 (OH), 1790 (C=O, trifluoroacetate), 1700-1730 (broad C=O vibration for an unchelated quinone), 1620 (chelated quinone) 1580 (C=C). UV: $\lambda_{max}$ (lgε)=247 (4.46), 282 (3.84), 456 (3.85), 480 (3.93), 512 (3.77), 553 nm (3.05). $^1$H-NMR: δ=1.10 (t; J=7.5 Hz; 3H, CH$_2$CH$_3$), 1.70 (dq, $J_{gem}$=24.9, J=7.5 Hz; 2H, CH$_2$CH$_3$), 1.85 (ddd, $J_{9a,9e}$=14.2, $J_{9a,10a}$=11.6, $J_{9a,10e}$=6.2 Hz; 1H, 9a—H), 2.11 (dddd, $J_{gem}$=14.2, $J_{9e, 10a}$=6.4, $J_{9e,10e}$=4.4, $J_{9e,7e}$=1.2 Hz; 1H, 9—H), 2.89 (ddd, $J_{gem}$=19.6, $J_{9a,10a}$=11.6, $J_{10a,9e}$=6.4 Hz; 1H, 10—H), 3.12 (ddd, $J_{gem}$=19.6, $J_{10e,9a}$=6.2, $J_{10e,9e}$=4.4 Hz; 1H, 10—H), 6.26 (d, $J_{9e,7e}$=1.2 Hz; 1H, 7—H), 7.83 (cm; 2H, 2—, 3—H), 8.33 (cm; 2H, 1—, 4—H), 13.31, 13.45 (each s; 1H each, each OH). MS (300° C.): m/e=450 (M+, 35%), 338 (9), 337 (14), 336 (47), 320 (14), 318 (23), 309 (22), 308 (100), 307 (29), 293 (15), 291 (13), 282 (11), 281 (34), 280 (24), 279 (45), 254 (19).

EXAMPLE 13

(+)-1-Deoxy-α$_1$-rhodomycinone (I, $R=CH_3$, $R_2=OH$, $R_4=H$, $R_5=OH$)

One drop of bromine was added to a solution of 100 mg (0.23 mmol) of trifluoroacetate (III, $R=CH_3$, $R_2=OCOCF_3$, $R_3=H$) in 20 ml of dry carbon tetrachloride at room temperature, and the solution was irradiated with a 100 W lamp for 2 hours. After 1 hour, another drop of bromine was added (TLC check). The solution was then evaporated in vacuo at room temperature, the residue was suspended in 10 ml of ether, and 5 ml of cold 1% strength sodium hydroxide solution was added, and the mixture was stirred for thmee minutes. After acidification with 6N hydrochloric acid, the mixture was extracted with dichloromethane, and the solution was dried over sodium sulfate and evaporated in vacuo. The residue was subjected to layer chromatography (dichloromethane/ether 96:4). 36 mg (34%) of triol crystallized from the polar main fraction and had melting point 143° C. (decomposition). IR: 3400 (OH), 1620 (chelated quinone), 1580 (C=C). UV: $\lambda_{max}$ (lgε)=223 (4.04), 245 (4.37), 278 (3.64), 319 (3.27), 448 (3.68), 478 (3.82), 513 nm (3.59), $^1$H-NMR: δ=1.53 (s; 3H, CH$_3$), 2.19 (ddd, $J_{gem}$=15.2, $J_{9e,10e}$=2.0, $J_{9e,7e}$=1.2 Hz; 1H, 9e—H), 2.26 (dd; $J_{gem}$=15.2, $J_{9a,10a}$=4.6 Hz; 1H, 9a—H), 2.76 (cm; 1H, OH), 3.46 (cm; 1H, OH), 3.51 (cm; 1H, OH), 4.84 (dd, $J_{7e,7-OH}$=4.8. $J_{7e,9e}$=1.2 Hz; 1H, 7e—H), 5.25 (cm; 1H, 10e—H), 7.86 (cm; 2H, 2—, 3-H), 8.37 (cm; 2H, 1—, 4—H), 13.44, 13.51 (each s; 1H each, each OH). MS (unheated): m/e=356 (M+, 3%), 338 (16), 336 (20), 321 (20), 320 (100), 305 (13), 304 (58), 298 (RDA, 27), 296 (14), 295 (17), 281 (11), 280 (61), 279 (10), 278 (23), 268 (11), 267 (16).

$C_{19}H_{16}O_7$ (356.3): calculated: C 64.04, H 4.53, found: C 63.73, H 4.62.

EXAMPLE 14

(+)-1-Deoxy-10-epi-α$_1$-rhodomycinone (I, $R=CH_3$, $R_2=OH$, $R_4=OH$, $R_5=H$)

1.5 mg (1.4%) of the 10-epi compound were obtained from the more polar zone of the chromatography (see above) and had melting point 120° C. IR: 3400 (OH), 1620 (chelated quinone), 1580 (C=C). UV: $\lambda_{max}$ (lgε)=228 (3.89), 250 (4.11), 282 (3.64), 317 (3.23), 459 (3.44), 482 (3.49), 502 (3.39), 512 (3.34), 550 nm (2.78). $^1$H-NMR: ε=1.52 (s; 3H, CH$_3$), 2.18 (dd, $J_{9a,9e}$=13.8, $J_{9a,10a}$=9.2 Hz; 1H, 9a—H), 2.34 (ddd, $J_{9a,9e}$=13.8, $J_{9e,10a}$=7.2, $J_{9e,7e}$=1.2 Hz; 1H, 9e—H), 3.68 (s; 1H, OH), 3.96 (s; 1H, OH), 4.16 (broad s; 1H, OH), 4.77 (d, $J_{9e,7e}$=1.2 Hz; 1H, 7e—H), 5.31 (dd, $J_{9a,10a}$=9.2, $J_{9e,10a}$=7.2 Hz; 1H, 10a—H), 7.87 (cm; 2H—, 3—H), 8.37 (cm; 2H, 1—, 4—H), 13.49 13.82 (each s; 1H each, each OH). MS (195° C.): m/e=338 (M—H$_2$O, 5%), 337 (13), 336 (61), 321 (19), 320 (M—2H$_2$O, 90%), 305 (13), 304 (70), 303 (13), 298 (RDA, 5), 280 (11), 189 (13).

EXAMPLE 15

(+)-1,7-Dideoxy-$\alpha_1$-7-rhodomycinonyl trifluoroacetate
(I, R=CH$_3$, R$_1$=H, R$_2$=OH, R$_5$=OH)

Prepared by the procedure according to Example 13. By acidification of the reaction solution after 30 seconds followed by layer chromatography (dichloromethane/ether 96:4), the following product ratio was obtained with increasing polarity: amount of trifluoroacetate used: 100 mg (0.23 mmol). Yield: title compound: 29 mg (28%), melting point 220° C.; triol (I, R=CH$_3$, R$_2$=OH, R$_5$=OH): 4 mg (14%).

Title compound: IR: 3350 (OH), 1790 (C═O, trifluoroacetate), 1630 (chelated quinone), 1585 (C═C). $^1$H-NMR: $\delta$=1.43 (s; 3H, CH$_3$), 2.19 (dd, J$_{gem}$=15.0, J$_{9a,10e}$=4.8 Hz; 1H, 9a—H), 2.37 (ddd, J$_{gem}$=15.0, J$_{9e,10e}$=1.7, J$_{9e,7e}$=1.5 Hz; 1H, 9e—H), 3.47 (broad signal: 1H, OH), 3.95 (broad signal; 1H, OH), 5.35 (dd, J$_{9a,10e}$=4.8, J$_{9e,10e}$=1.7 Hz; 1H, 10e—H), 6.35 (d, J$_{9e,7e}$=1.5 Hz; 1H, 7e—H), 7.87 (cm; 2H, 2—3—H), 8.36 (cm; 2H, 1—, 4—H), 13.21, 13.41 (each s; 1H each, each OH). MS (130° C.): m/e=452 (M$^+$, 27%), 434 (11), 338 (43), 322 (13), 321 (27), 320 (100), 305 (23), 304 (60), 303 (11), 296 (14), 295 (25), 294 (16), 293 (12), 292 (27), 291 (12), 281 (30), 280 (63), 279 (16), 278 (43), 277 (33), 268 (13), 297 (19).

EXAMPLE 16

(+)-1-Deoxy-$\beta$-rhodomycinone (I, R=C$_2$H$_5$, R$_1$=H, R$_2$=OH, R$_3$=H, R$_4$=H, R$_5$=OH)

As described in Example 13, 36 mg (0.08 mmol) of trifluoroacetate (III, R=C$_2$H$_5$, R$_1$=H, R$_2$=OCOCF$_3$, R$_3$=H) were brominated and hydrolyzed with sodium hydroxide solution. After layer chromatography, 8 mg (30%) of triol (title compound) were obtained from the polar main fraction and had melting point 212° C. $^1$H-NMR: $\delta$=1.13 (T, J=7.4 Hz; 3H, CH$_2$CH$_3$), 1.78 (dq, J$_{gem}$=15.0, J=7.4 Hz; 1H, CH$_2$CH$_3$), 1.91 (dq, 1H, CH$_2$CH$_3$), 2.15 (dd, J$_{gem}$=15.2, J$_{9a,10e}$=4.4 Hz; 1H, 9a—H), 2.23 (ddd, J$_{gem}$=15.2, J$_{9e,10e}$=2.8, J$_{9e,7e}$=1.3 Hz; 1H, 9e—H), 3.32 (s, exchangeable with CD$_3$OD; 1H, 8—OH), 3.49 (d exchangeable; J$_{10e,10-OH}$=3.6 Hz; 1H, 10—OH), 3.65 (d exchangeable, J$_{7e,7-OH}$=1.2 Hz; 1H, 7—OH), 4.91 (dd, J$_{7e,7-OH}$=1.2, J$_{9e,7e}$=1.3 Hz; 1H, 7e—H), 5.23 (dd-d, J$_{10e,9a}$=4.4, J$_{10e,10-OH}$=3.6, J$_{10e,9e}$=2.8 Hz; 1H, 10e—H), 7.87 (cm; 2H, 2—, 3—H), 8.38 (cm; 2H, 1—, 4—H), 13.46, 13.51 (each s; 1H each, each OH). MS (175° C.): m/e=371 (M+1, 4%), 370 (M$^+$, 19), 353 (18), 352 (77), 350 (14), 335 (19), 334 (65), 318 (22), 299 (18), 298 (RDA, 100), 297 (20), 296 (94), 295 (66), 281 (27), 280 (93), 278 (41), 277 (15), 270 (16), 269 (10), 268 (26), 267 (31), 252 (11).

C$_{20}$H$_{18}$O$_7$ (370.4): calculated: C 64.86, H 4.90, found: C 64.62, H 4.99.

EXAMPLE 17

2-Formyl-6,11-dihydroxy-2-methyl-2H,3,4,7,12-tetrahydroanthra[1,2-b]pyran-7,12-dione (IV)

50 mg of (II, R=CH$_3$, R$_1$=OH) were added to 10 ml of a 1 percent sodium ethanolate solution at 20° C. After stirring under nitrogen for 45 minutes, the mixture was diluted with 50 ml of dichloromethane, acidified with cold 6N hydrochloric acid and, after addition of 100 ml of water, was extracted. The organic phase was washed twice with water, dried over sodium sulfate, filtered and the solvent was removed in vacuo. After layer chromatography (dichloromethane/ether 95:5), 33 mg (80%) crystallized out of the polar fraction and had melting point 228° C. (decomposition). IR: 1725 (aldehyde), 1610 (chelated quinone) cm$^{-1}$. UV: $\lambda_{max}$ (lg$\epsilon$)=231 (4.59), 246 (4.20), 288 (3.93), 417 (3.64), 480 nm (4.04). $^1$H-NMR: $\delta$=1.60 (s; 3H, CH$_3$), 1.98 (dddd, J$_{gem}$=14.0, J$_{3a,4a}$=8.8, J$_{3a,4e}$=6.9, J$_{3a,CHO}$=1.0 Hz; 1H, 3a—H), 2.34 (dt, J$_{gem}$=14.0, J$_{3e,4a,e}$=6.0 Hz; 1H, 3e—H), 283 (dddd, J$_{gem}$=18.4, J$_{4a,3a}$=8.8, J$_{4a,3e}$=6.0, J$_{4a,5}$=1.2 Hz; 1H, 4a—H), 2.90 (dddd, J$_{gem}$=18.4, J$_{4e,3a}$=6.9, J$_{4e,3e}$=6.0, J$_{4e,5}$=1.2 Hz; 1H, 4e—H), 7.07 (t, J$_{4,5}$=1H, 5—H), 7.30 (dd, J$_{9,10}$=8.2, J$_{8,10}$=1.2 Hz; 1H, 10—H), 7.63 (dd, J$_{9,10}$=8.2, J$_{8,9}$=7.6 Hz; 1H, 9—H), 7.80 (dd, J$_{8,9}$=7.6, J$_{8,10}$=1.2 Hz; 1H, 8—H), 9.76 (d, J$_{3a,CHO}$=1.0 Hz; 1H, CHO), 13.11, 13.17 (each s; 1H each, each OH).

C$_{19}$H$_{14}$O$_6$ (228.3): calculated: C 67.45, H 4.17, found: C 67.34, H 4.11.

EXAMPLE 18

7-Deoxy-$\beta_1$-rhodomycinone (III, R=CH$_3$, R$_1$=OH, R$_2$=R$_3$=H)

20 mg (0.06 mmol) of (IV) were dissolved in 5 ml of methanol and, under nitrogen, 10 ml of 1N sodium hydroxide solution were added. A sodium dithionite solution was added dropwise at room temperature until the color changed from blue to yellow-orange, and the mixture was stirred overnight. It was stirred in air for reoxidation (30 minutes). The solution was then diluted with 30 ml of water and acidified with cold 6N hydrochloric acid until the color changed to red. It was extracted twice with 20 ml of dichloromethane each time, and the solution was washed with water, dried over sodium sulfate, filtered and the solvent was removed in vacuo. The crude product was subjected to layer chromatography (dichloromethane ether 95:5). 8 mg (40%) of IV crystallized out of the polar fraction and had melting point 225° C. (decomposition). IR: 3400 (OH), 1600 (chelated quinone), 1585 (C═C) cm$^{-1}$. UV: $\lambda_{max}$ (lg$\epsilon$)=232 (4.35), 253 (4.36), 291 (3.78), 433sh, 459 (3.91), 475 (3.95), 488 (4.03), 510 (3.86), 522 nm (3.89). $^1$H-NMR: $\delta$=1.46 (s; 3H, CH$_3$), 1.77 (dt, J$_{gem}$=13.8, J=8.0 Hz, 1H, 9a—H), 1.98 (d-dt, J$_{gem}$=13.8, J=5.2, J$_{9e,7e}$=2.0 Hz; 1H, 9e—H), 2.36 (broad signal: 1H, OH), 2.78 (dd, J$_{gem}$=18.6, J$_{7e,9e}$=2.0 Hz; 1H, 7e—H), 2.95 (cm; 2H, 10—H$_2$), 2.99 (d broad; J$_{gem}$=18.6 Hz; 1H, 7a—H), 7.29 (dd, J$_{2,3}$=8.4, J$_{2,4}$=1.2 Hz; 1H, 2—H), 7.70 (t; 1H, 3—H), 7.87 (dd, J$_{3,4}$=7.6, J$_{2,4}$=1.2 Hz; 1H, 4—H), 12.30, 12.83, 13.65 (each s; 1H each, each OH). MS (220° C.): m/e=341 (M+1, 21%), 340 (M$^+$, 100), 323 (13), 322 (48), 307 (40), 298 (18), 297 (42), 283 (23), 282 (RDA, 81), 279 (18), 278 (12).

If the experimental conditions indicated above were modified, using an amount of 25 mg of IV, it was possible at room temperature to obtain exclusively the deoxy compound (title compound) (20 mg-80%) after 2 hours. If the batch was cooled to 0° C. before the reduction to the leuco form, using 35 mg of IV, then the trans-diol (III, R=CH$_3$, R$_1$=OH, R$_2$=OH) (22 mg, 63%) and cis-diol (III, R=CH$_3$, R$_1$=OH, R$_3$=OH) (10 mg, 25%) were obtained.

EXAMPLE 19

(+)-8c-n-Propyl-7,8,9,10-tetrahydro-1,6,7r,8t,11-pentahydroxy-5,12-naphthacenequinone = 13-homo-rhodomycinone (III, R=n—$C_3H_7$, $R_1$=OH, $R_2$=OH, $R_3$=H)

30 ml of 0.2N NaOH solution were added to a solution of 100 mg (0.23 mmol) of II (R=n—$C_3H_7$) in 30 ml of dichloromethane. After addition of a spatula tip of tetrabutylammonium hydrogen sulfate, the mixture was stirred until the starting material had completely reacted (II, R=n—$C_3H_7$, $R_1$=OH) (about 1 hour; TLC check). The mixture was cooled in ice and, under nitrogen, was reduced with a solution of 100 mg of sodium dithionite in 5 ml of water. After stirring for 30 minutes while cooling in ice, air was passed through the solution for reoxidation (about 20 minutes), then it was acidified with dilute hydrochloric acid and extracted twice with 30 ml of dichloromethane each time. The organic phase was washed twice with water, dried over sodium sulfate, filtered and evaporated. The residue was subjected to layer chromatography (dichloromethane/ether 90:10). 57 mg (65%) of trans-diol (title compound) crystallised out of the non-polar fraction from the chromatography and had melting point 219° C. (decomposition). IR: 3450 (OH), 2945-2850 (CH), 1600 (chelated quinone), 1500 (C=C) cm$^{-1}$. UV: $\lambda_{max}$ (lg$\epsilon$)=220 sh, 235 (4.41), 252 (4.34), 290 (3.77), 435sh, 466 (394), 479 (3.98), 491 (4.06), 510 (3.91), 525 nm (3.92). MS (290° C.): m/e=384 (M$^+$, 44%), 368 (24), 366 (M—$H_2O$, 16), 350 (13), 349 (12), 348 (M—$2H_2O$, 40), 337 (12), 319 (16), 307 (11), 298 (RDA, 44), 297 (18), 296 (27), 295 (50), 285 (10), 284 (14), 283 (13), 282 (18), 271 (16), 270 (87), 269 (12), 255 (11).

$C_{21}H_{20}O_7$ (384.4): calculated: C 65.62, H 5.24, found: C 65.41, H 5.29.

EXAMPLE 20

(+)-8t-n-Propyl-7,8,9,10-tetrahydro-1,6,7r,8c,11-pentahydroxy-5,12-naphthacenequinone (III, R=n—$C_3H_7$, $R_1$—=OH, $R_2$=H, $R_3$=OH)

20 mg (23%) of cis-diol (title compound) crystallized out of the polar fraction from the chromatography (see above) and had melting point 169° C. IR: 3360 (OH), 2950-2850 (CH), 1600 (chelated quinone, C=C) cm$^{-1}$. UV: $\lambda_{max}$(lg$\epsilon$)=218sh, 233 (4.43), 251 (4.31), 291 (3.78), 464 (3.94), 477 (3.99), 491 (4.06), 511 (3.92), 525 (3.90). $^1$H-NMR (400 MHz): $\delta$=0.95 (t, J=7.0 Hz; 3H, $CH_3$), 1.54 (cm; 4H, $CH_2CH_2CH_3$), 1.76 (ddd, $J_{gem}$=13.5, $J_{9a,10a}$=12.9, $J_{9a,10e}$=$\overline{6.3}$ Hz; 1H, 9a—H), 2.09 (ddd, $J_{gem}$=13.5, $J_{9e,10a}$=7.2 Hz, $J_{9e,10e}$=5.8 Hz; 1H, 9e—H), 2.74 (dt, $J_{gem}$=19.4, J=6.6 Hz; 1H, 10—H), 2.79 (s; 1H, 8—OH), 3.02 (dt, $J_{gem}$=19.4, J=6.2 Hz; 1H, 10—H), 3.75 (d, J=2.0 Hz; 1H, 1—OH), 4.80 (broad s; 1H, 7a—H), 7.32 (dd, $J_{2,3}$=8.4, $J_{4,2}$=1.1 Hz; 1H, 2—H), 7.71 (t; 1H, 3—H), 7.89 (dd, $J_{3,4}$=7.4, $J_{2,4}$=1.1 Hz; 1H, 4—H), 12.25, 12.75, 14.07 (each s; 1H each, each OH). MS (240° C.): m/e=385 (M+1, 18%), 384 (M$^+$, 76), 366 (27), 348 (14), 337 (11), 298 (RDA, 52), 296 (34), 295 (56), 285 (11), 271 (18), 270 (100), 203 (13).

EXAMPLE 21

(+)-$\gamma$-Rhodomycinone (III, R=$C_2H_5$, $R_1$=OH, $R_2$=OH) and (+)-7-epi-$\gamma$-rhodomycinone (III, R=$C_2H_5$, $R_1$=OH, $R_3$=OH)

218 mg (59%) trans-diol and 81 mg (22%) cis-diol, which were identical to reference samples prepared earlier, were obtained from 425 mg (1 mmol) of dichloride (II, R=$C_2H_5$, $R_1$=OH) in analogy to the procedure described in Example 19.

EXAMPLE 22

(+)-7-Deoxy-13-homo-$\gamma$-7-rhodomycinonyl trifluoroaceate (III, R=n—$C_3H_7$, $R_1$=OH, $R_2$=OCOCF$_3$)

50 mg (0.13 mmol) of trans-diol (III, R=n—$C_3H_7$, $R_1$=OH, $R_2$=OH) were converted into the monotrifluoroacetate (III, $R_2$=OCOCF$_3$) as described in Example 12. Yield: 62 mg (quantitative); melting point 171° C. IR: 3475 (OH), 2950-2840 (CH), 1790 (C=O, trifluoroacetate), 1680 (quinone), 1600 (chelated quinone) cm$^{-1}$. UV: $\lambda_{max}$ (lg$\epsilon$)=222sh, 233 (4.43), 252 (4.33), 291 (3.84), 464 (3.95), 479 (4.00), 490 (4.06), 509 (3.93), 524 nm (3.91). $^1$H-NMR: $\delta$=1.00 (dt, J=6.6, J=1.8 Hz; 3H, $CH_3$), 1.59 (cm; 4H, $CH_2CH_2CH_3$), 1.86 (ddd, $J_{gem}$=13.9, $J_{9a,10}$=11.6, $J_{9a,10e}$=$\overline{6.0}$ Hz; 1H, 9a—H), 2.11 (cm; 1H, 9e—H), 2.88 (ddd, $J_{gem}$==19.3, $J_{9a,10a}$=11.6, $J_{10a,9e}$=6.0 Hz; 1H, 10a—H), 3.09 (cm; 1H, 10e—H), 6.24 (d, $J_{9e,7e}$=1.2 Hz; 1H, 7e—H), 7.31 (dd, $J_{2,3}$=8.4, $J_{2,4}$=1.0 Hz; 1H, 2—H), 7.71 (t; 1H, 3—H), 7.87 (dd, $J_{3,4}$=7.6, $J_{2,4}$=1.0 Hz; 1H, 4—H), 12.15, 12.67, 13.56 (each s; 1H each, each OH). MS (250° C.): m/e=480 (M$^+$, 12%). 366 (29), 348 (12), 339 (20), 338 (94), 323 (15), 309 (20), 297 (15), 296 (14), 295 (24), 270 (19), 203 (13).

EXAMPLE 23

13-Homo-$\beta$-rhodomycinone (I, R=n-$C_3H_7$, $R_1$=OH, $R_2$=OH, $R_5$=OH 30 mg (0.06 mmol) of trifluoroacetate according to Example 20 were hydroxylated by process described for Example 13 to give 8 mg (30%) of title compound of melting point 218° C. (decomposition). $^1$H-NMR: $\delta$=1.03 (t, J=7.2 Hz; 3H, $CH_3$), 1.48-1.84 (m; 4H, $CH_2CH_2CH_3$), 2.16 (dd, $J_{gem}$=15.0, $J_{9a,10e}$=4.0 Hz; 1H, 9a—H), 2.23 (ddd, $J_{gem}$=15.0, $J_{9e,10e}$=1.6, $J_{9e,7e}$=1.0 Hz; 1H, 9e—H), 2.67 (broad signal; 1H, OH), 3.31 (broad s; 1H, OH), 3.66 (s; 1H, OH), 4.86 (d, $J_{9e,7e}$=1.0 Hz; 1H, 7e—H), 5.22 (cm; J/2=9.2 Hz, 10e—H), 7.34 (dd, $J_{2,3}$=8.6, $J_{2,4}$=1.0 Hz; 1H, 2—H), 7.73 (t; 1H, 3—H), 7.90 (dd, $J_{3,4}$=7.2, $J_{2,4}$=1.0 Hz; 1H, 4—H), 12.12, 12.87, 13.58 (each s; 1H each, each OH). MS (200° C.): m/e=400 (M$^+$, 9%), 384 (19), 383 (12), 382 (48), 380 (27), 366 (11), 365 (13), 364 (45), 349 (13), 348 (46), 335 (18), 319 (18), 315 (14), 314 (RDA, 78), 313 (18), 312 (82), 311 (55), 298 (19), 297 (22), 296 (77), 295 (25), 294 (31), 293 (12), 286 (15), 285 (11), 284 (18), 283 (21), 270 (32).

$C_{21}H_{20}O_8$ (400.4): calculated: C 63.00, H 5.03, found: C 62.89, H 5.12.

EXAMPLE 24

13-Homo-$\gamma$-rhodomycinone (I, R=n-$C_3H_7$, $R_1$=OH, $R_2$=OH, $R_4$=OH)

A solution of 6 mg of 13-homo-$\beta$-rhodomycinone Example 21) in 1 ml of trifluoroacetic acid was allowed to stand at room temperature for 24 hours, then, with stirring, 20 ml of 1N NaOH were added, and the mixture was acidified with dilute hydrochloric acid after one minute and extracted with dichloromethane. The solvent was removed in vacuo and the residue was subjected to layer chromatography (dichloromethane/methanol 98:2). 3 mg of the starting material was recovered from the less polar zone, and 0.5 mg of triol (title compound) was obtained from the polar zone and had melting point 207° C. (decomposition). $^1$H-NMR: $\delta=1.00$ (cm; 3H, CH$_3$), 1.40–1.70 (m; 4H, CH$_2$CH$_2$CH$_3$), 2.30 (cm; 2H, 9a, e—H), 4.77 (cm; 1H, 7—H), 5.44 (cm; 1H, 10—H), 7.34 (d broad; J$_{2,3}$=8.5 Hz; 1H, 2—H), 7.73 (t; 1H, 3—H), 7.90 (d broad; J$_{3,4}$=7.6 Hz; 1H, 4—H), 12.09, 13.16, 13.60 (each s; 1H each, each OH). MS (175° C.): m/e=400 (M+, 6%), 384 (15, 382 (31), 380 (27), 366 (12), 365 (11), 364 (39), 351 (11), 349 (17), 348 (64), 335 (15), 323 (11), 319 (30), 314 (49), 313 (11), 312 (44), 311 (30), 298 (15), 297 (18), 296 (67), 295 (23), 294 (23), 293 (10), 291 (11), 286 (15), 284 (13), 283 (15), 270 (40).

We claim:

1. A process for the preparation of a compound of the formula I

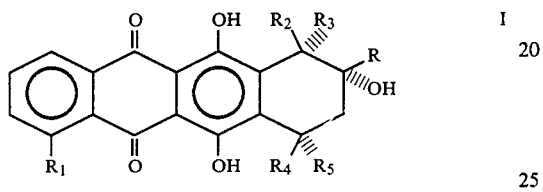

in which R denotes C$_1$–C$_4$-alkyl, R$_1$ denotes hydrogen or hydroxyl, R$_2$ and R$_3$ differ from one another and each denote hydrogen or hydroxyl, and R$_4$ and R$_5$ like from one another and denote hydrogen or hydroxyl, which process comprises taking a compound of the formula

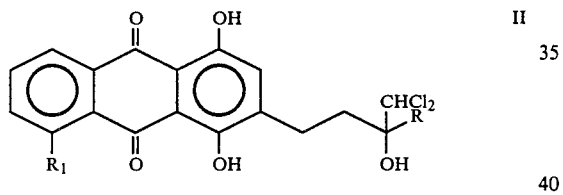

in which R and R$_1$ have the above-mentioned meaning, and either (a) where R$_1$ denotes hydrogen, reacting it with an alkali metal hydroxide solution with the addition of a reduction agent at 0° C. and then oxidizing the resulting product with air and acidifying, whereupon a compound of the formula III

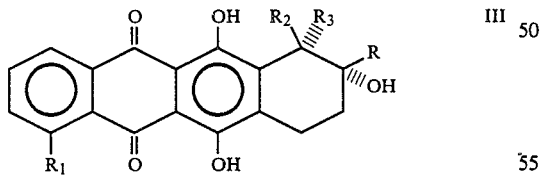

in which R$_1$ denotes hydrogen and R, R$_2$ and R$_3$ have the above-mentioned meaning, is obtained or (b) where R$_1$ denotes the OH group, reacting it in a phase-transfer reaction with an alkali metal hydroxide solution in a chlorinated hydrocarbon, with the addition of tetrabutylammonium hydrogen sulfate, followed by reduction with a reducing agent at 0° C. to give a compound of the formula III, in which R$_1$ denotes the OH group and R$_1$, R$_2$ and R$_3$ have the above-mentioned meaning, or (c) where R$_1$ denotes the OH group and R denotes CH$_3$, reacting it with an alkali metal methanolate at room temperature under an inert gas to give a compound of the formula IV

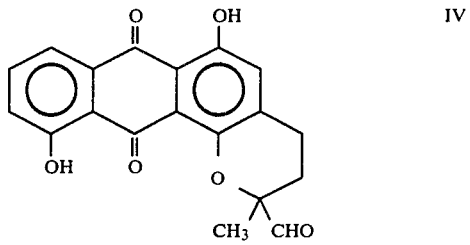

and converting the resulting cyclic aldehyde, by reaction with a reducing agent at 0° C. followed by oxidation with air and acidification, into a compound of the formula III, in which R denotes CH$_3$, R$_1$ denotes the OH group and R$_2$ and R$_3$ have the above-mentioned meaning, and (d) converting a compound of the formula III, in which R, R$_1$ and R$_3$ have the above-mentioned meaning, and R$_2$ denotes the OH group by esterification with hexafluoroacidic anhydride into a compound of the formula III, in which R$_2$ represents the —OCOCF$_3$ radical, and (e) brominating a compound of the formula III, in which R and R$_1$ have the above-mentioned meaning, R$_3$ represents hydrogen and R$_2$ represents the —OCOCF$_3$ radical; and then carrying out hydrolysis to give a compound of the formula I.

2. The process for the preparation of a compound of the formula I as claimed in claim 1, wherein a compound of the formula II

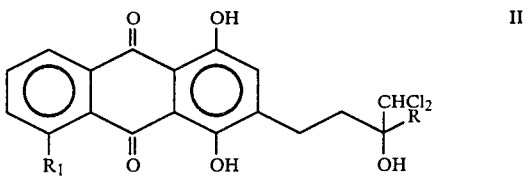

in which R denotes C$_1$–C$_{14}$-alkyl, is reacted in a phase-transfer reaction with an alkali metal hydroxide solution in dichloromethane, with the addition of tetrabutylammonium hydrogen sulfate, followed by reduction with sodium dithionite at 0° C. to give a compound of the formula III

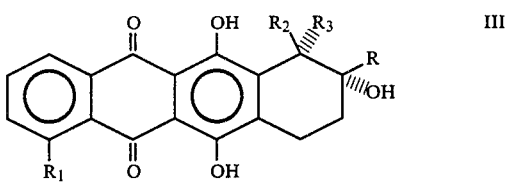

in which R, R$_2$ and R$_3$ have the meanings indicated in claim 1, the resulting compound of the formula III, in which R$_2$ denotes an OH group, is converted with hexafluoroacetic anhydride into a compound of the formula III, in which R$_2$ represents the —OCOCF$_3$ radical, and the resulting compound is brominated and then hydrolyzed.

3. A compound of the formula II

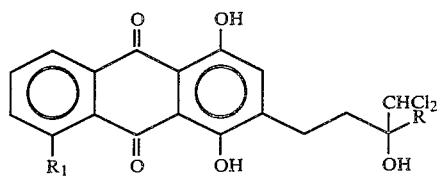
in which R represents $C_1$–$C_4$-alkyl and $R_1$ represents hydrogen or hydroxyl.
4. The process for the preparation of a compound of formula I as claimed in claim 1 wherein the reducing agent is sodium dithionite.
5. The process for the preparation of a compound of formula I as claimed in claim 1 wherein the chlorinated hydrocarbon is dichloromethane.
* * * * *